United States Patent [19]

Long

[11] Patent Number: 4,857,736
[45] Date of Patent: Aug. 15, 1989

[54] WAXY BUILDUP MEASUREMENT

[75] Inventor: Thomas E. Long, Houston, Tex.

[73] Assignee: Shell Oil Company, Houston, Tex.

[21] Appl. No.: 39,826

[22] Filed: Apr. 15, 1987

Related U.S. Application Data

[63] Continuation of Ser. No. 750,398, Jun. 28, 1985, abandoned.

[51] Int. Cl.$^4$ ............................................. G01N 23/04
[52] U.S. Cl. .................................. 250/358.1; 378/59; 378/54
[58] Field of Search ................. 250/358.1; 378/54, 58, 378/59

[56] References Cited

U.S. PATENT DOCUMENTS

| | | | |
|---|---|---|---|
| 2,957,987 | 10/1960 | Arnesen | 250/358.1 |
| 2,999,932 | 9/1961 | Spooner | 250/358.1 |
| 3,108,186 | 10/1963 | Flavel, Jr. | 250/358.1 |
| 3,582,647 | 6/1971 | Fignet | 250/358.1 |

FOREIGN PATENT DOCUMENTS

| | | | |
|---|---|---|---|
| 0160324 | 6/1983 | Fed. Rep. of Germany | 250/358.1 |
| 01020156 | 7/1983 | Japan | 250/358.1 |

*Primary Examiner*—Carolyn E. Fields
*Assistant Examiner*—Richard Hanig

[57] ABSTRACT

The present invention provides an accurate measurement of the waxy buildup in pipeline by injecting an X-ray opaque material into the pipeline, then X-raying the line at three or more points in order to get an average wax thickness.

11 Claims, 1 Drawing Sheet

WAXY BUILDUP MEASUREMENT

This is a continuation of application Ser. No. 750,398, filed June 28, 1985 now abandoned.

BACKGROUND OF THE INVENTION

Certain crude oils contain a high concentration of wax. When such crude oils are transported by pipeline, a layer of wax rapidly forms on the inside wall of the pipeline which eventually can result in plugging of the line. Accordingly, it is necessary that such pipelines be cleaned out, usually by pigging, more or less frequently depending upon the concentration of wax in the crude oil being transported and the tendency of the wax to deposit. Cleaning pipelines is expensive, not only from the standpoint of the cost of pigging, etc. but also from the standpoint of sometimes having to shut down the line. Accordingly, it is desirable to only perform cleaning on an "as needed" basis, rather than on a set cycle based on predicted waxy buildup in the pipeline. This requires a testing procedure to quickly and inexpensively determine the extent of waxy buildup in the pipeline. At this time, the art does not provide such a testing procedure for waxy buildup which meets these qualifications.

Applicant is not aware of any prior art which, in his judgment as one skilled in the pipeline art, would anticipate or render obvious this novel measurement technique of the present invention.

SUMMARY OF THE INVENTION

The primary purpose of the present invention is to provide a measurement technique which accurately and efficiently measures the buildup of wax, resins, polymers and the like in pipelines, vessels and other containers. Accordingly, the present invention provides a method and apparatus for carrying out the method, for determining the amount of radiation-transparent material, such as wax, deposited inside a container of a fluid bearing the radiation transparent material, such as a pipeline, comprising: disposing a radiation-opaque material, such as barium solution, inside the container; providing a radiation source outside the container, such as an X-ray emitting apparatus; and positioning a radiation receptor, such as film, on the opposite side of the container from the radiation source. The thickness of the wax layer can then be determined by measuring the distance between a shadow cast by the wall of the container on the film and a shadow cast by the radiation-opaque material.

Other purposes, distinctions over the art, advantages and features of the invention will be apparent to one skilled in the art upon review of the following.

DESCRIPTION OF PREFERRED EMBODIMENTS

Figure 1:
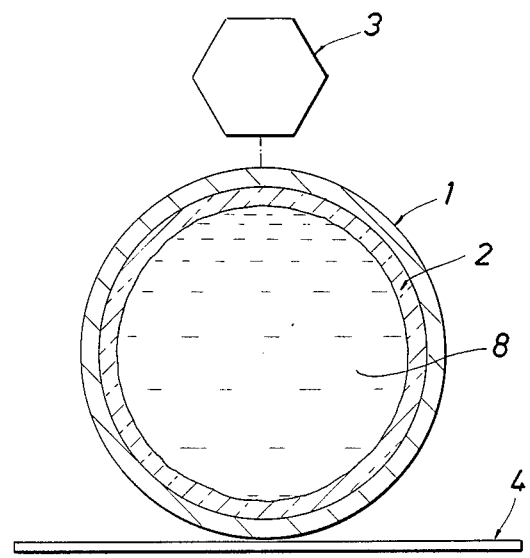
FIGS. 1 and 2 show end and longitudinal views of a pipeline with an X-ray source and X-ray film located on opposite sides thereof.
Figure 2:
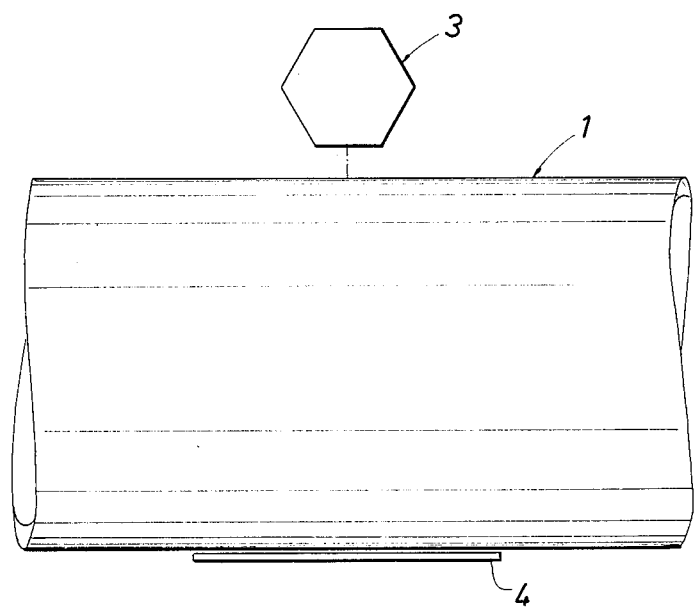

Referring now to FIGS. 1 and 2 of the invention, which are end and longitudinal views of the pipeline, there is a pipe wall 1 having a wax layer 2 therewithin. On one side of the pipe wall 1 there is provided a radiation source 3, which may be a source of X-rays, gamma rays, or other radiation suitable for the present invention. On the other side of the pipe 1 from the X-ray source there is provided a radiation receptor, such as X-ray film 4, or other material suitable to receive the radiation passing through the pipeline. Alternatively to the use of film, a fluoroscopic screen will provide immediate viewing of the thickness of the wax inside the pipeline. Within the pipeline and inside the wax layer 2 a radiation-opaque material 8, such as a barium solution or the like, is provided either separately or in admixture with the fluid which is being transported, such as waxy crude oil. The invention is suitable not only for determining the deposition of wax, but also other radiation-transparent materials such as resins, polymers and the like.

Figure 3:
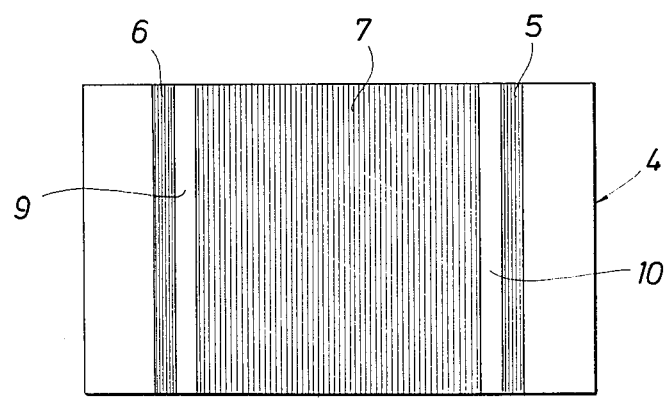
FIG. 3 is an exposed X-ray film.

In FIG. 3 there is shown the effects of the radiation passing through the pipe wall 1 and striking the X-ray film 4. The pipe wall 1 casts shadows 5 and 6 at the edge of the film due to the extra distance the X-rays must pass in going through the pipe wall at its extremities. The entire pipe, in fact, to some extent clouds the entire image on the film all the way from shadow 6 to shadow 5. The radiation-opaque material 8 is shown as the central large shadow 7. Between the shadow 7 and the shadows 5 and 6 is shown the shadows 9 and 10 of the radiation transparent material which are discernably lighter in comparison to shadows 5, 6 and 7. Measuring either shadow 9 or 10 gives the wax thickness. X-raying the pipeline at three or more points will get an average wax thickness.

The foregoing description of the invention is merely intended to be explanatory thereof, and various changes in the details of the described method and apparatus may be made within the scope of the appended claims without departing from the spirit of the invention.

What is claimed is:

1. A method for determining the amount of radiation transparent material deposited inside a container of a fluid bearing the radiation transparent material, comprising:
    disposing a radiation-opaque material inside the container;
    providing a radiation source outside the container;
    positioning a radiation receptor film on the opposite of the container from the radiation source; and
    measuring the distance on the film between a shadow cast by a wall of the container and a shadow cast by the radiation-opaque material to determine the thickness of radiation transparent material deposited on the container.

2. The method of claim 1 including emitting X-rays from the radiation source through the container.

3. The method of claim 2 wherein the radiation receptor is X-ray film which is exposed to the X-rays from the radiation source.

4. The method of claim 1 wherein the container is a pipeline and the pipeline is radiated in at least three different locations to determine an average thickness of radiation transparent material deposited inside the pipeline.

5. An apparatus for determining the amount of radiation transparent material deposited inside a container of a fluid bearing the radiation transparent material, comprising:
    means for disposing a radiation-opaque material inside the container;
    means for providing a radiation source outside the container;

means for positioning a radiation receptor film on the opposite side of the container from the radiation source; and means for measuring the distance on the film between a shadow cast by a wall of the container and a shadow cast by the radiation-opaque material to determine the thickness of radiation transparent material deposited on the container.

6. The apparatus of claim 5 wherein the radiation source is a means for emitting X-rays and the radiation receptor is X-ray film.

7. The apparatus of claim 6 wherein the container is a pipeline.

8. The apparatus of claim 5 wherein the radiation source is a means for emitting gamma rays.

9. The apparatus of claim 5 wherein radiation-opaque material is barium solution.

10. A method for determining the amount of radiation transparent material deposited inside a container of a fluid bearing the radiation transparent material, comprising:

disposing a radiation-opaque material inside the container;

providing a radiation source outside the container;

positioning a radiation receptor on the opposite side of the container from the radiation source; and measuring the distance on the receptor between a shadow cast by a wall of the container and a shadow cast by the radiation-opaque material to determine the thickness of radiation transparent material deposited on the container.

11. An apparatus for determining the amount of radiation transparent material deposited inside a container of a fluid bearing the radiation transparent material, comprising:

means for disposing a radiation-opaque material inside the container;

means for providing a radiation source outside the container;

means for positioning a radiation receptor on the opposite side of the container from the radiation source; and means for measuring the distance on the receptor between a shadow cast by a wall of the container and a shadow cast by the radiation-opaque material to determine the thickness of radiation transparent material deposited on the container.

* * * * *